United States Patent
Owen et al.

(10) Patent No.: US 11,607,194 B2
(45) Date of Patent: Mar. 21, 2023

(54) ULTRASOUND IMAGING SYSTEM WITH DEPTH-DEPENDENT TRANSMIT FOCUS

(71) Applicant: KONINKLIJKE PHILIPS N.V., Eindhoven (NL)

(72) Inventors: Neil Owen, Bothell, WA (US); Changhong Hu, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 644 days.

(21) Appl. No.: 16/365,775

(22) Filed: Mar. 27, 2019

(65) Prior Publication Data
US 2019/0298309 A1 Oct. 3, 2019

Related U.S. Application Data

(60) Provisional application No. 62/648,436, filed on Mar. 27, 2018.

(51) Int. Cl.
A61B 8/00 (2006.01)
A61B 8/08 (2006.01)

(52) U.S. Cl.
CPC .............. *A61B 8/463* (2013.01); *A61B 8/467* (2013.01); *A61B 8/5207* (2013.01)

(58) Field of Classification Search
CPC . G01S 15/8927; A61B 8/4488; A61B 8/4494; A61B 2017/22027–22028; A61B 8/54
See application file for complete search history.

(56) References Cited

U.S. PATENT DOCUMENTS

| | | | | |
|---|---|---|---|---|
| 5,462,057 A * | 10/1995 | Hunt | ............... | G01S 7/52046 600/447 |
| 5,677,491 A * | 10/1997 | Ishrak | ............... | A61B 8/4494 73/628 |
| 5,882,309 A * | 3/1999 | Chiao | ............... | G01S 7/52046 600/459 |
| 5,931,785 A * | 8/1999 | Mason | ............... | B06B 1/0629 600/459 |
| 6,057,632 A * | 5/2000 | Ustuner | ............... | B06B 1/0622 310/334 |
| 6,132,374 A * | 10/2000 | Hossack | ............... | G01S 7/52038 600/443 |

(Continued)

FOREIGN PATENT DOCUMENTS

EP  373603 B1 * 3/1995 ........... B06B 1/0622

*Primary Examiner* — Joel Lamprecht
*Assistant Examiner* — Nyrobi Celestine

(57) ABSTRACT

An ultrasound system includes a transducer array having three or more rows of transducer elements extending in the azimuth dimension and located adjacent to each other in the elevation dimension. The rows have different mechanical foci in the elevation dimension, with an inner row elevationally focused in the near field and outer rows elevationally focused in the far field. When the user is imaging a subject in the near field, the system beamformer transmits with the inner row with a near field elevation focus. When imaging in the far field a plurality of rows elevationally focused in the far field are used for transmission. When the user is imaging in the mid-range, the beamformer uses both the inner row and the plurality of outer rows to provide an extended mid-range elevation focus.

16 Claims, 6 Drawing Sheets

(56) References Cited

U.S. PATENT DOCUMENTS

| | | | | |
|---|---|---|---|---|
| 6,544,179 B1* | 4/2003 | Schmiesing | ........ | G01S 7/52046 600/447 |
| 6,629,929 B1* | 10/2003 | Jago | .................... | G01S 7/52046 600/443 |
| 7,263,888 B2* | 9/2007 | Barshinger | .......... | G01N 29/262 73/587 |
| 2003/0233046 A1* | 12/2003 | Ferguson | ............. | A61B 8/0833 600/437 |
| 2004/0044284 A1* | 3/2004 | Von Behren | ........ | G01S 7/52046 600/444 |
| 2006/0052699 A1* | 3/2006 | Angelsen | ............ | G01S 7/52042 600/437 |
| 2007/0167752 A1* | 7/2007 | Proulx | ................ | G01S 15/8925 600/437 |
| 2008/0033293 A1* | 2/2008 | Beasley | ................. | A61B 8/465 600/437 |
| 2008/0255456 A1* | 10/2008 | Kye | ....................... | G10K 11/32 600/459 |
| 2009/0043195 A1* | 2/2009 | Poland | ................... | A61B 8/461 600/437 |
| 2009/0240148 A1* | 9/2009 | Jeong | ....................... | A61N 7/02 600/439 |
| 2010/0004539 A1* | 1/2010 | Chen | ...................... | A61B 8/462 600/445 |
| 2012/0289830 A1* | 11/2012 | Halmann | ............... | A61B 8/463 600/443 |
| 2015/0148674 A1* | 5/2015 | Park | ....................... | A61B 8/485 600/438 |
| 2015/0333800 A1* | 11/2015 | Perry | ................... | G10K 11/346 320/108 |
| 2017/0128046 A1* | 5/2017 | Kim | ....................... | G10K 11/34 |
| 2019/0224501 A1* | 7/2019 | Burdette | .................. | A61N 7/02 |

* cited by examiner

ULTRASOUND IMAGING SYSTEM WITH DEPTH-DEPENDENT TRANSMIT FOCUS

CROSS-REFERENCE TO RELATED APPLICATION

The present application claims priority to and the benefit of U.S. Provisional Application Ser. No. 62/648,436, filed Mar. 27, 2018, which is hereby incorporated by reference herein.

This invention relates to ultrasound imaging systems and, in particular, to ultrasound imaging systems with depth-dependent transmit focus control.

Ultrasound imaging systems with array transducers are capable of focusing both the transmitted ultrasound waves and the received echo signals at desired depths of focus. This is done by phased timing of the actuation of the transducer elements of the active aperture on transmit, and phased delay of echoes received by elements of the active aperture before they are combined to complete receive beam formation. During reception of echo signals the delays applied to the echoes received by different transducer elements can be continually varied as echoes are received from increasing depths of field, enabling the focal depth to be continually changed, a process known as dynamic focusing. With dynamic focusing, received echoes are focused at the exact depths from which they are received. But transmit focusing is only possible for a single depth of focus. That is because, once the ultrasound waves are launched into the subject from the elements of the transmit aperture, the ultrasound system can no longer affect their relative times of transmission. Advanced ultrasound systems such as the Epiq line of ultrasound systems available from Philips Healthcare of Andover, Mass., USA are able to synthesize the effect of dynamic transmit focusing by means of a beamformer which performs parallel processing of multiple receive lines from differently focused transmit beams. But for conventional ultrasound systems, the laws of physics allow transmit beams to be focused at only a single depth of field.

The traditional way to produce an ultrasound image which is transmit-focused at multiple depths of field is known as zone focusing. In zone focusing, multiple partial images are transmitted and received with different depths of transmit focus. The partial images are then "spliced" together to form a single image with different transmit focal ranges. For instance, a first image can be transmitted and received at a focal depth of 4 cm. Second and third images can be transmitted and received with focal ranges centered around 6 cm and 8 cm. Horizontal strips of the three images are then combined to produce a single image which is transmit focused at 4, 6, and 8 cm. But zone focusing comes at a cost, which is a reduction in the frame rate of display, since three separate transmit-receive cycles are necessary to produce the single zone-focused image. Instead of producing live images at a 30 Hz frame rate of display, the zone focused images can be produced at only a 10 Hz frame rate in this example. This results in temporal jitter or blurring of rapidly moving objects such as live images of a beating heart.

An adaptive technique for determining transmit focal depths automatically is described in U.S. Pat. No. 6,544,179 (Schmiesing et al.) The ultrasound systems described in this patent are able to analyze the content of acquired ultrasound images and respond by invoking both correctly located and the optimal number of focal depths for a given ultrasound exam. This optimizes the image quality in regions of an image which are generally of interest to a clinician. See also U.S. Pat. No. 6,629,929 (Jago et al.)

The foregoing techniques are all directed toward focusing transmit beams in the azimuth plane, the plane of a two-dimensional (2D) image. When a clinician views a 2D image on an ultrasound display, the clinician has the impression that the image is of a cut plane through the subject. But the planar image in fact has a finite thickness which is determined by the geometric and operating characteristics of the transducer. For example, if a blood vessel passes through the image plane normal to the plane, the clinician would expect to see the vessel lumen as a circle in the image. If the vessel passes through the image plane at an acute angle, the vessel lumen should appear oval. But if the image plane has an appreciable thickness, echoes are acquired from a segment of the blood vessel, which will cause the vessel lumen and its boundaries to appear blurred or indistinct. This is not an artifact of azimuthal focusing, but of the thickness of the image plane in the elevation dimension. Several approaches have been used to minimize the problem by reducing the acoustic thickness of the image plane. One is to form a cylindrical lens on the faces of the transducer elements, so that each element is geometrically focused at a nominal focal depth. The image plane will be thinnest at the nominal depth and anatomy at that depth in the image will have less blurring due to plane thickness. See, e.g., U.S. Pat. No. 3,936,791 (Kossoff). Another approach which is available with a 2D array is to electronically focus the beam in the elevation dimension. While both approaches provide a single focal point or range in the elevation dimension where the image plane will be at its thinnest, the focal point of a 2D array can be electronically adjusted in depth by phased timing of the transmit pulses applied to elements aligned in the elevation dimension, whereas the geometric lens of the one-dimensional (1D) array can only have a single fixed focal point. Accordingly, it would be desirable to provide selectable elevation focus while retaining a high frame rate of display for real time ultrasonic imaging.

In accordance with the principles of the present invention, an ultrasound system is described which uses a transducer array with multiple rows of transducer elements capable of providing selectable elevation focusing for highly resolved ultrasound images. The transducer array has three or more parallel rows of transducer elements and the multiple rows are employed in different combinations to provide different elevation focal characteristics. In an illustrated implementation the array has three rows of transducer elements, with the inner row having a mechanical focus in the elevation dimension which provides elevation focusing at a shallow focal point. The two outer rows have a mechanical focus in the elevation dimension which, when combined with the inner row focus, provides elevation focusing at a deeper focal point. When the inner row and full aperture are operated sequentially in a zone focus mode, elevation focus is provided at both the shallow and deep focal points. The ultrasound system responds to selection by a user of a location of interest and invokes the optimal elevation focus, which affords a high frame rate of display when only a single elevation focus is necessary and a lower frame rate of display when multiple elevation focal points or an extended focal range are required.

Figure 1:
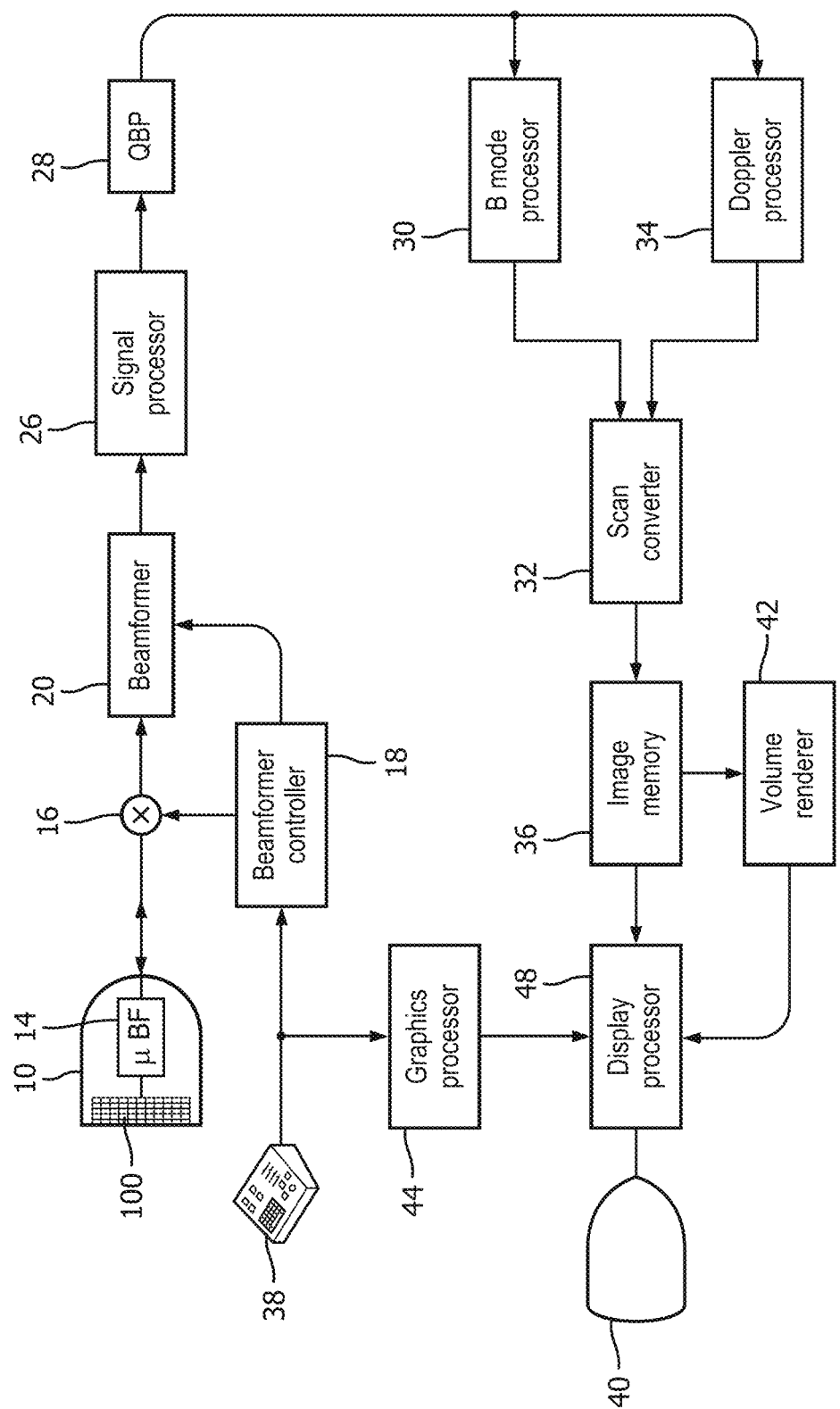
FIG. 1 illustrates in block diagram form an ultrasound system configured in accordance with the principles of the present invention.

Referring now to FIG. 1, an ultrasound imaging system constructed in accordance with the principles of the present invention is shown in block diagram form. A transducer array 100 is provided in an ultrasound probe 10 for transmitting ultrasonic waves and receiving echo information. The transducer array 100 has three or more rows of transducer elements as described more fully in FIGS. 2 and 2a. The transducer array 100 can be coupled to a system beamformer 20 for operation of the array, but in a preferred implementation the array elements are coupled to a microbeamformer 14 in the probe which controls transmission and reception of signals by the array elements. The use of the microbeamformer reduces the number of signal lines in the cable between the probe and the system mainframe. The microbeamformer is coupled by the probe cable to a transmit/receive (T/R) switch 16 which switches between transmission and reception and protects the system beamformer 20 from high energy transmit signals. The transmission of ultrasonic beams from the transducer array 12 under control of the microbeamformer 14 (or the beamformer, in the absence of a microbeamformer) is directed by a beamformer controller 18 coupled to the T/R switch and the system beamformer 20, which receives input from the user's operation of the user interface or control panel 38 of the ultrasound system. Among the transmit characteristics controlled by the transmit controller are the number, spacing, amplitude, phase, frequency, polarity, and diversity of transmit waveforms. For operation in accordance with the present invention the beamformer controller also controls, via the beamformer or microbeamformer, the number of rows of transducer elements which are used for beam transmission as described more fully below. Beams formed in the direction of pulse transmission may be steered straight ahead from the transducer array, or at different angles in azimuth on either side of an unsteered beam by phased actuation of transducer elements for a wider sector field of view. In a preferred implementation the transducer array is operated as a linear array whereby a group of adjacent elements is selected for the active aperture of a beam and the active aperture is stepped across the array in the azimuth direction by the beamformer or microbeamformer to scan successive adjacent beams across an image field. The echoes received by a group of transducer elements are beamformed by appropriately delaying them and then combining them in the system beamformer 20 to form a sequence of coherent echo signals from along each beam direction.

The coherent echo signals undergo signal processing by a signal processor 26, which includes filtering by a digital filter and noise reduction as by spatial or frequency compounding. The filtered echo signals are coupled to a quadrature bandpass filter (QBP) 28. The QBP filter performs three functions: band limiting the RF echo signal data, producing in-phase and quadrature pairs (I and Q) of echo signal data, and decimating the digital sample rate. The QBP filter comprises two separate filters, one producing in-phase samples and the other producing quadrature samples, with each filter being formed by a plurality of multiplier-accumulators (MACs) implementing an FIR filter. The signal processor can also shift the frequency band to a lower or baseband frequency range, as can the QBP filter. The digital filter of the signal processor 26 can be a filter of the type disclosed in U.S. Pat. No. 5,833,613 (Averkiou et al.), for example.

The beamformed and processed coherent echo signals are coupled to a B mode processor 30 which produces a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format for linear array scanning or a sector display format for phased array scanning. Either the B mode image or the Doppler image may be displayed alone, or the two shown together in anatomical registration in which the color Doppler overlay shows the blood flow in tissue and vessels of the B mode image. Another display possibility is to display side-by-side images of the same anatomy which have been processed differently. This display format is useful when comparing images.

The image data produced by the B mode processor 30 and the Doppler processor 34 are coupled to an image data memory 36, where it is stored in memory locations addressable in accordance with the spatial locations from which the image values were acquired. Image data from 3D scanning with a 2D array can be accessed by a volume renderer 42, which converts the echo signals of a 3D data set into a projected 3D image as viewed from a given reference point as described in U.S. Pat. No. 6,530,885 (Entrekin et al.) The 3D images produced by the volume renderer 42 and 2D images produced by the scan converter 32 are coupled to a display processor 48 for further enhancement, buffering and temporary storage for display on an image display 40. Graphical information such as patient ID entered by the user from the control panel 38 and other graphics such as a location of interest box positioned by a user over the image as described below are produced by a graphics processor 44, and an overlay of the graphics with the image is produced for presentation by the display processor 48.

Figure 2:
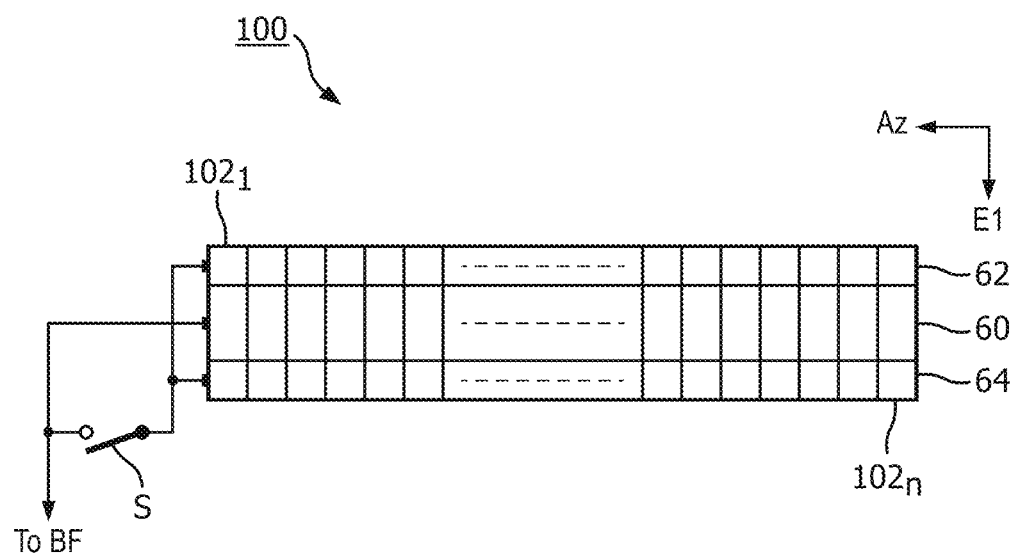
FIG. 2 is a plan view of a 1.XD transducer array constructed in accordance with the principles of the present invention.
Figure 2A:
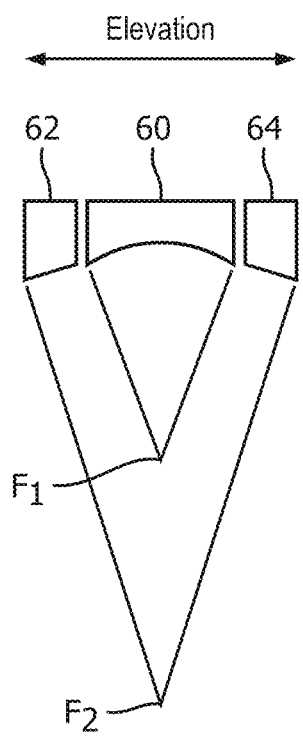
FIG. 2a is an end view of the three rows of transducer elements of the array of FIG. 2, illustrating the different mechanical elevation foci of the inner and outer row elements.

FIG. 2 illustrates one example of a transducer array 100 in plan view and constructed in accordance with the principles of the present invention. The transducer array has three or more rows of transducer elements and may be a 1.XD array or a full 2D array. While a 2D array can steer and focus beams in any direction in all three dimensions, a 1.XD array uses its additional rows of elements for elevation focusing to determine the thickness of a scan plane normal to the face of the array. The illustrated array 100 with three rows is known as a 1.25D array, which scans an image plane normal to the face of the array, with the outer rows providing controllable elevation focusing for plane thickness control. The azimuth (Az) and elevation (El) directions are noted adjacent to the array. An example transducer array will have 128 columns of elements $102_1$ to $102_n$ where n is equal to 128 and thus be suitable for operation by a standard 128-channel beamformer. The array 100 is seen to have an inner row of elements 60 and two outer rows 62 and 64 of elements. In one mode of operation, the inner row of element is operated alone and the array thus functions as a 1D array, with whatever geometric elevation focus characteristic the inner row possesses. The faces of the elements of the inner row can exhibit a cylindrical curvature in the elevation direction as shown in FIG. 2*a*, causing these elements to have a fixed geometric focus in the elevation direction at a depth of F1 as shown in the drawing and illustrated in the aforementioned Kossoff patent. Alternately, elements with a planar (flat) face can be affixed with a cylindrical-shaped acoustic lens, which provides the same result. The outer rows of elements 62 and 64 exhibit a different mechanical focus, such as a curvature with a greater radius which causes the outer rows in conjunction with the inner row to focus at a greater depth as illustrated by the depth of focal point F2 in FIG. 2*a*. For operation of the rows individually or separately, each vertical column of elevationally disposed elements of the array of FIG. 2 is wired as shown to the left of the drawing. When switch S is open, only the elements of the inner row are actuated, and when switch S is closed, all three elements, the full elevational aperture, are operated together. Each column of three elements is separately wired as shown, so that each element or elevational group of elements in the azimuth direction is separately controllable and operated, so that beams of the array can be steered and focused in azimuth by selection or phased operation in the azimuth dimension.

Figure 3:
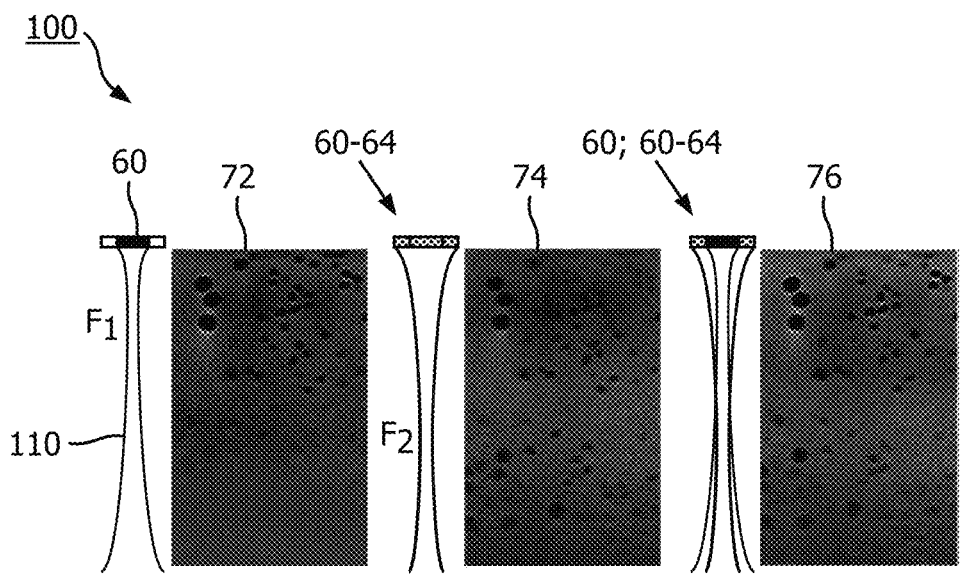
FIG. 3 illustrates three ultrasound images acquired by operation of the transducer array of FIG. 2 in three different scanning modes and the respective elevation beam profiles.

In accordance with the principles of the present invention, the array 100 is operable in three different modes for different elevation focus control. FIG. 3 shows the array 100 in an end view of the three rows in elevation, and a resultant image produce by operation in the respective mode. At the left side of FIG. 3, only the inner row 60 is actuated for transmission, and the array is operated in the manner of a 1D (single row) array. The geometric (mechanical) focus of the elements of the inner row produces beams with a near field elevation focus at depth $F_1$, as shown by the profile 110 of a beam in the elevation dimension. The resultant image 72 is seen to be sharply focused in the near field close to the array, and exhibits relatively poorer focus in the far field (at greater depth). In the second mode of operation in the center of the drawing, all three rows 62-60-64 are operated together; the full elevation aperture is used. The beam profile of the full aperture is seen to have a geometric focus $F_2$ at a greater depth, as seen by the sharp focus in the far field in resultant image 74. The third mode of operation is shown at the right of the drawing, and is produced by execution of the two previous modes in succession. The inner row 60 is operated to produce a beam with a near field focus, and all three rows are operated together to produce a beam with a far field focus. Following each beam transmission, echoes are received from the near field and the far field, respectively, and stored in the image memory. The near and far field echoes from both beams across the array are then combined in a single image by the display processor, producing an image which is thus well focused in elevation in both the near and far fields, as illustrated by the combined elevation beam profile shown to the left of resultant image 76. Scanning can be done by acquiring echoes from the skinline to a given depth and then from the given depth to a maximum depth, then joining the two images together at the given depth. Preferably, echoes are acquired in the near and far fields which overlap in the mid-range, so that mid-range echoes from both images can be combined by weighted blending as described in U.S. Pat. No. 6,283,919 (Roundhill et al.), eliminating a possible seam artifact in the mid-field.

But the drawback of the third mode, unlike the first and second modes, is that it requires transmission and reception of two beams at each beam position, in effect, multi-zone focusing. The need to transmit twice at each beam location thus doubles the time needed to acquire the image data and thus halves the frame rate of display. In accordance with a further aspect of the present invention, the third mode is invoked by the ultrasound system only when it is deemed necessary, so that a higher frame rate of display for live imaging is used as much as possible.

Figure 4:
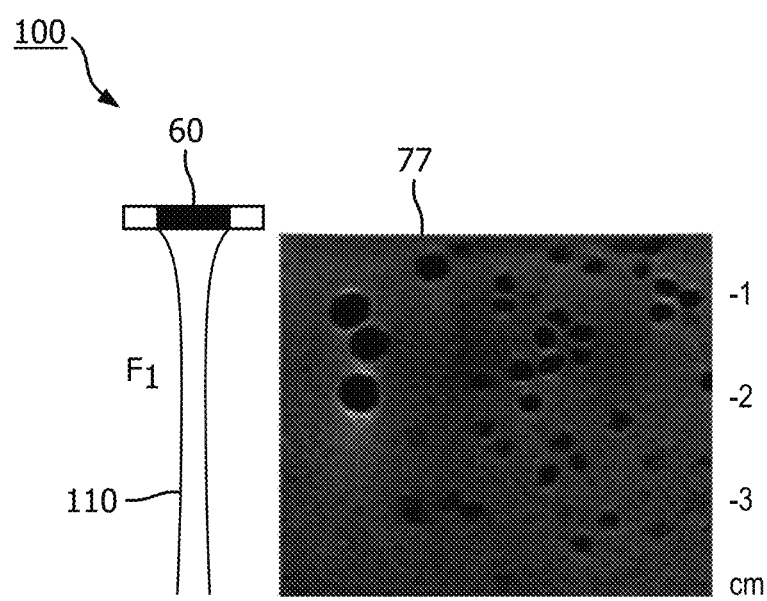
FIG. 4 illustrates the selection of the inner row of elements for scanning when imaging in the near field and a resultant near field image.
Figure 5:
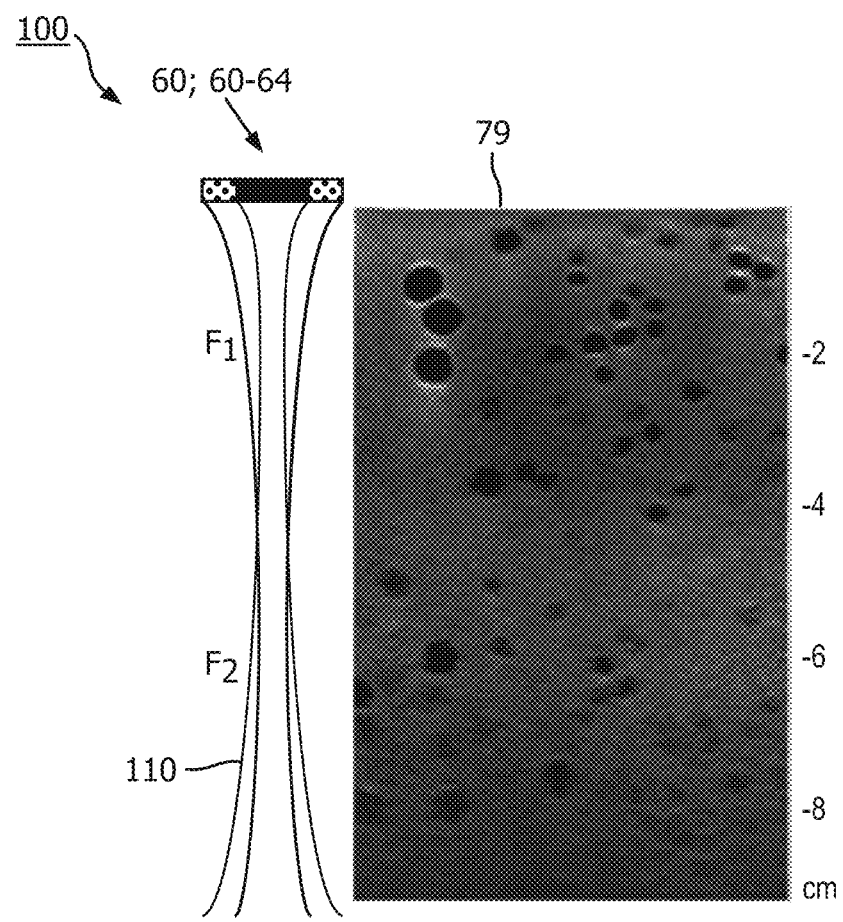
FIG. 5 illustrates the selection of the inner row and full aperture for scanning, providing an extended range of elevation focus between two focal points and a resultant extended depth focused image.

This selective use of the third mode is accomplished by monitoring the user's use of the ultrasound system. By monitoring the depths of anatomy of interest to the user, the third mode is only invoked when the extended or intermediate elevation focus is beneficial for imaging the anatomy of interest to the user. For example, the system can monitor the depth of the center of the image, which is known by the beamformer controller since the depth setting selected by the user sets the maximum depth from which the beamformer is to receive and process echo signals. Since many users will set the image depth so that the anatomy of interest is in the center of the image, the system can respond by using the mode of operation which optimizes the elevation focus at the depth of the center of the image. An example of this technique is shown in FIGS. 4 and 5. In FIG. 4, the user has manipulated the image depth control of the user interface so that a near field image 77 is produced, extending from the skinline down to about 4 cm. Since the user has chosen to produce an image of only the near field, the first mode of transducer operation is automatically used by the beamformer controller to provide an optimal elevation focus, and the beamformer controller responds to this depth setting by using only the inner row 60 of the array to produce beams with an elevation focus at F1, which is around a depth of 2 cm. Since only a single beam is transmitted at each beam location across the image field, the resultant images will be produced at a relatively high frame rate of display for high quality real time images.

In FIG. 5 the user has set the depth of the image to extend beyond 8 cm, with the center of the image at around a depth of 4-6 cm. The beamformer controller responds to this image depth setting by operating the transducer array in the third mode, with both the inner row and the full elevation aperture used to scan the image field. The resultant image 79 will thus exhibit an optimal extended focus in the mid-range, through the center of the image. While this will decrease the frame rate of display due to the need to transmit twice to acquire a full line of echoes, the tradeoff is improved image quality at the depth of interest to the user.

Figure 6:
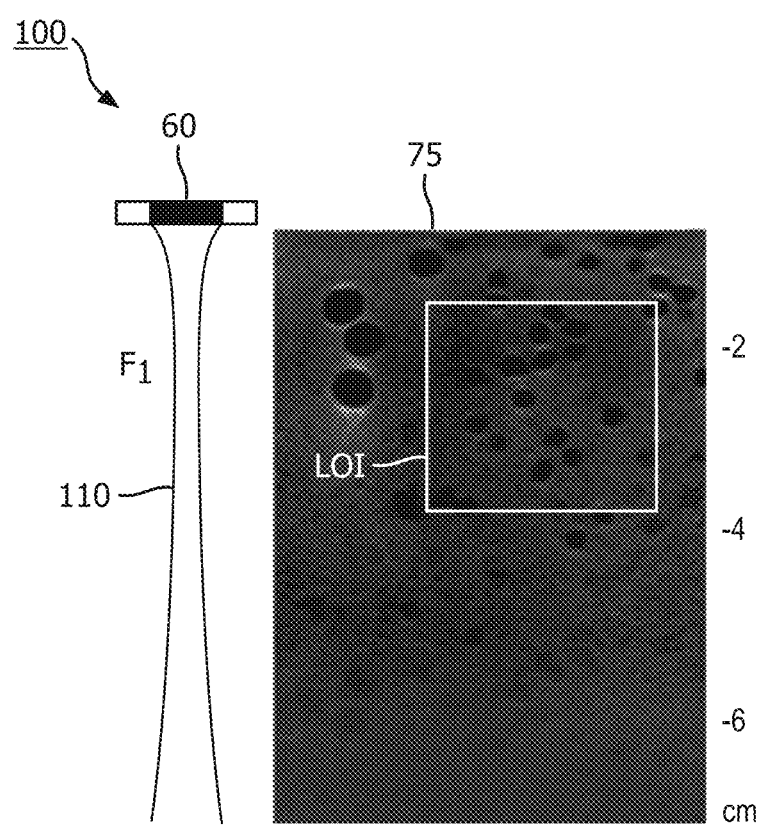
FIG. 6 illustrates the selection of the inner row of elements for scanning when a location of interest in the near field is identified by a user.
Figure 7:
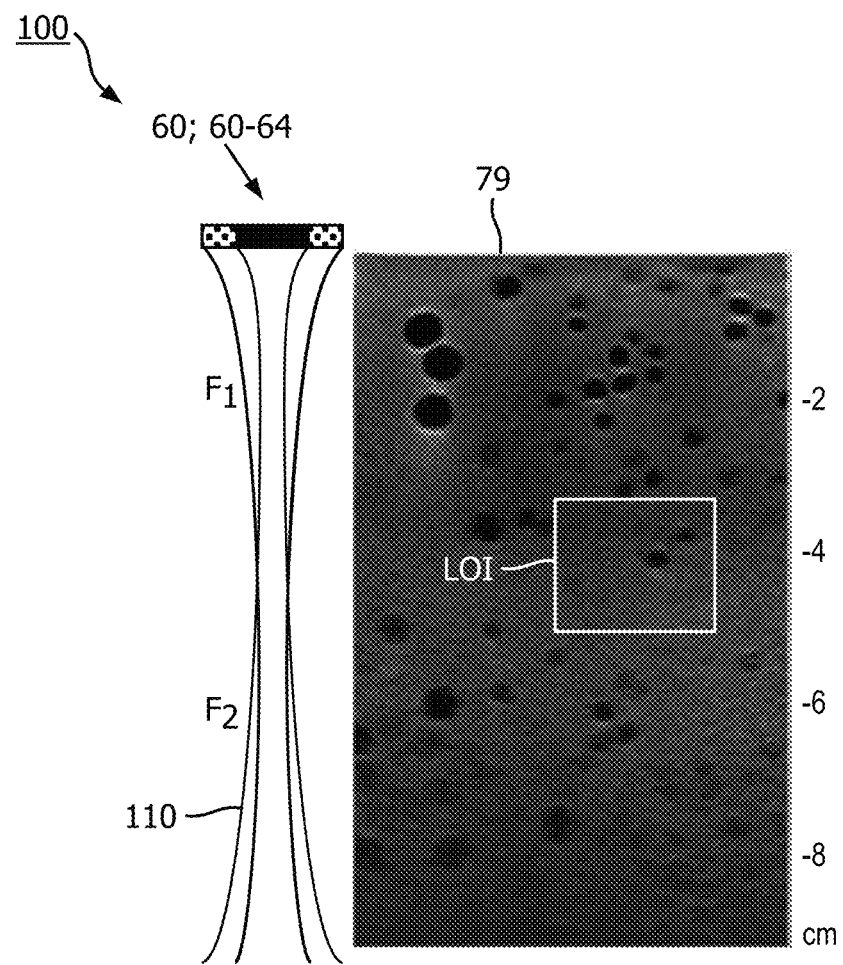
FIG. 7 illustrates the selection of both the inner row and full aperture for producing an image with an extended elevation focus when a mid-range location of interest is identified by a user.

FIGS. 6 and 7 illustrate the use of a user-positioned location of interest box LOI to indicate the depth of interest. The user actuates the LOI box control on the user interface 38 to generate a graphic box over the image, then manipulates a user interface control such as a trackball to position the LOI box over the anatomy of interest. In the example of FIG. 6, the user has positioned the LOI box over anatomy in the near field of image 75, at a depth of 2-3 cm. The beamformer controller responds to this positioning of the LOI box by operating the array 100 in the first mode, using only the inner row 60 of the array for beam transmission. The resultant elevation focal point $F_1$ around 2-3 cm thereby provides optimal elevation focus for the depth of this near field anatomy in the LOI box.

In FIG. 7, the user has positioned the LOI box in image 79 at a depth around 4 cm. The beamformer controller responds to this positioning of the LOI box by operating array 100 in the third mode, which produces an extended elevation focus around an intermediate depth of 4 cm. The inner row 60 and then the full elevation aperture 60-64 are used to transmit two beams at each beam location, and the received echoes are blended together in the mid-range to produce an extended optimal elevation focus around a depth of 4 cm. The frame rate of display has been reduced, but the benefit is improved resolution of the anatomy outlined by the LOI box.

When the user positions the LOI box at a greater depth such as 6-8 cm, the beamformer controller operates the array in the second mode, using the full elevation aperture of rows 60-64 to produce an optimal elevation focus, a thin image plane, at the greater depth of interest.

It should be noted that an ultrasound system suitable for use in an implementation of the present invention, and in particular the component structure of the ultrasound system of FIGS. 1, 2, and 2a, may be implemented in hardware, software or a combination thereof. The various embodiments and/or components of an ultrasound system, for example, the beamformer controller and the display processor, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as the image memory 36 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a beamformer control module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound system providing elevation focus control comprising:

an array transducer comprising at least three adjacent rows of transducer elements, including an inner row and outer rows, each row extending in an azimuth dimension and the rows being adjacent in an elevation dimension, wherein faces of the transducer elements of the inner row comprise a cylindrical curvature in the elevation dimension and faces of the transducer elements of the outer rows comprise a curvature in the elevation dimension, wherein a radius of the curvature is different than a radius of the cylindrical curvature;

a beamformer coupled to the array transducer and adapted to transmit beams from the array transducer in different modes using different rows of transducer elements, wherein each mode produces beams exhibiting a predetermined elevation focal depth, wherein the beamformer is further adapted to beamform received echo signals and form coherent echo signals;

an image processor coupled to receive the coherent echo signals and adapted to produce an ultrasound image;

a user control adapted to indicate a depth of interest in the ultrasound image; and a beamformer controller, coupled to the beamformer and the user control, and adapted to (1) monitor and respond to a depth of the center of the ultrasound image and to (2) respond to the depth of interest indicated by the user control, the response comprising selecting an appropriate transmit mode to thereby control the beamformer to transmit beams from the array transducer with an elevation focal depth which is optimal for a depth of interest.

2. The ultrasound system of claim 1, wherein the user control is further adapted to indicate a depth of interest by setting a displayed image depth.

3. The ultrasound system of claim 2, wherein the beamformer controller is further adapted to control the beamformer to transmit beams with an elevation focal depth at or around the center of the ultrasound image.

4. The ultrasound system of claim 1, wherein the user control is further adapted to indicate a depth of interest by positioning a location of interest graphic in the ultrasound image.

5. The ultrasound system of claim 4, wherein the beamformer controller is further adapted to control the beamformer to transmit beams with an elevation focal depth at or around a depth of the location of interest graphic.

6. The ultrasound system of claim 5, wherein the different transmit beam modes further comprise transmit beams with different elevation foci.

7. The ultrasound system of claim 1, wherein the beamformer is further adapted to transmit beams from the array transducer in a first mode using only the inner row of transducer elements.

8. The ultrasound system of claim 7, wherein the beams transmitted in the first mode exhibit a near field elevation focus depth.

9. The ultrasound system of claim 7, wherein the beamformer is further adapted to transmit beams from the array transducer in a second mode using the inner row and outer rows of transducer elements.

10. The ultrasound system of claim 9, wherein the beams transmitted in the second mode exhibit a far field elevation focus depth.

11. The ultrasound system of claim 9, wherein the beamformer is further adapted to transmit beams from the array transducer in the second mode using a full elevation aperture.

12. An ultrasound system providing elevation focus control comprising:

an array transducer comprising at least three adjacent rows of transducer elements, including an inner row and outer rows, each row extending in an azimuth dimension and the rows being adjacent in an elevation dimension, wherein faces of the transducer elements of the inner row comprise a cylindrical curvature in the elevation dimension and faces of the transducer elements of the outer rows comprise a curvature in the elevation dimension, wherein a radius of the curvature is different than a radius of the cylindrical curvature;

a beamformer coupled to the array transducer and adapted to transmit beams from the array transducer in a first mode using the inner row of transducer elements, a second mode using the inner and outer rows of transducer elements, and a third mode using the first and second modes sequentially, wherein each mode produces beams exhibiting a predetermined elevation focal depth;

a display processor adapted to combine echoes from the sequential use of the first and second modes when the beamformer is operating in the third mode; and a beamformer controller, coupled to the beamformer and adapted to control the beamformer to transmit beams from the array transducer with an elevation focal depth which is optimal for a depth of interest.

13. The ultrasound system of claim 12, wherein the beams transmitted in the third mode exhibit an extended focal region between near field and far field elevation focal depths.

14. The ultrasound system of claim 12, wherein transducer elements of the inner row further exhibit a mechanical elevation focal depth in a near field.

15. The ultrasound system of claim 12, wherein transducer elements the outer row further exhibit a mechanical elevation focal depth in a far field.

16. The ultrasound system of claim 12, wherein the beamformer is further adapted to transmit beams from the array transducer in the third mode using the inner row of transducer elements for a first transmission at a near field beam focus and the inner and outer rows of transducer elements for a second transmission at a far field beam focus.

* * * * *